US006820866B2

(12) United States Patent
Mason

(10) Patent No.: US 6,820,866 B2
(45) Date of Patent: Nov. 23, 2004

(54) ATTENUATOR APPARATUS

(75) Inventor: James D. Mason, Las Vegas, NV (US)

(73) Assignee: Goodbar LLC, Las Vegas, NV (US)

( * ) Notice: Subject to any disclaimer, the term of this patent is extended or adjusted under 35 U.S.C. 154(b) by 0 days.

(21) Appl. No.: 10/215,149

(22) Filed: Aug. 7, 2002

(65) Prior Publication Data

US 2003/0030196 A1 Feb. 13, 2003

Related U.S. Application Data

(60) Provisional application No. 60/311,318, filed on Aug. 10, 2001.

(51) Int. Cl.[7] .................................................. F16F 5/00
(52) U.S. Cl. ................. 267/122; 267/64.23; 267/64.27; 188/269; 623/27
(58) Field of Search ................................. 267/172, 119, 267/130, 64.23, 64.26, 64.27; 157/317, 313, 269; 623/27, 35, 28, 37, 26

(56) References Cited

U.S. PATENT DOCUMENTS

| | | | | |
|---|---|---|---|---|
| 2,393,627 A | * | 1/1946 | Garand ......................... | 89/193 |
| 2,679,192 A | | 5/1954 | Seeley et al. | |
| 3,018,694 A | | 1/1962 | Browning | |
| 3,140,085 A | * | 7/1964 | Bourcier De Carbon | 267/64.23 |
| 3,316,558 A | * | 5/1967 | Mortensen .................. | 188/317 |
| 3,469,661 A | * | 9/1969 | Hoffman et al. ............ | 188/269 |
| 3,588,064 A | * | 6/1971 | Montanari ............... | 267/64.26 |
| 3,656,400 A | | 4/1972 | Stoner | |
| 3,779,131 A | | 12/1973 | Kawamura | |
| 3,944,197 A | * | 3/1976 | Dachicourt .............. | 267/64.23 |
| 4,880,213 A | * | 11/1989 | Shinbori et al. ......... | 267/64.27 |
| 5,092,902 A | | 3/1992 | Adams et al. | |
| 5,098,071 A | | 3/1992 | Umetsu | |
| 5,123,194 A | | 6/1992 | Mason | |
| 5,888,214 A | | 3/1999 | Ochoa | |
| 5,948,021 A | * | 9/1999 | Radcliffe ..................... | 188/287 |
| 5,961,556 A | * | 10/1999 | Thorn ......................... | 623/27 |
| 6,227,098 B1 | | 5/2001 | Mason | |
| 6,302,918 B1 | * | 10/2001 | Gramnas ..................... | 623/27 |

FOREIGN PATENT DOCUMENTS

| | | |
|---|---|---|
| DE | 162935 | 10/1905 |
| DE | 714566 | 2/1941 |
| DE | 1082810 | 6/1960 |
| DE | 1126747 | 3/1962 |
| FR | 2672355 | 2/1991 |
| GB | 418497 | * 10/1934 |
| WO | PCT/US 02/25234 | 3/2002 |

* cited by examiner

*Primary Examiner*—Matthew C. Graham
*Assistant Examiner*—Mariano Sy
(74) *Attorney, Agent, or Firm*—Gordon & Rees LLP

(57) ABSTRACT

An attenuator apparatus has an outer housing with a first chamber filled with a first fluid, and a bellows member of elastomeric material mounted in the first chamber and having a second chamber filled with a second fluid, the bellows member having a first end facing away from the first chamber. A piston is slidably mounted in the housing at the first end of the bellows member for acting on the bellows member in response to a force applied to the piston so as to expand the bellows member in the first chamber and cushion the force. The bellows member returns to its original configuration and biases the piston back in a second direction opposite to the first direction on removal of the force.

15 Claims, 7 Drawing Sheets

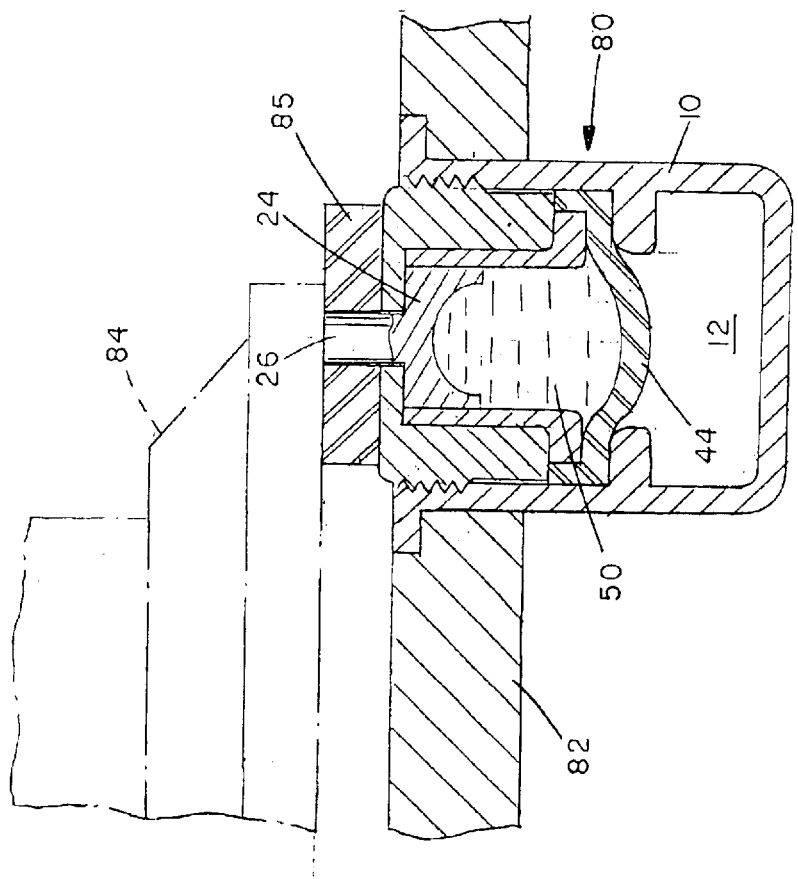
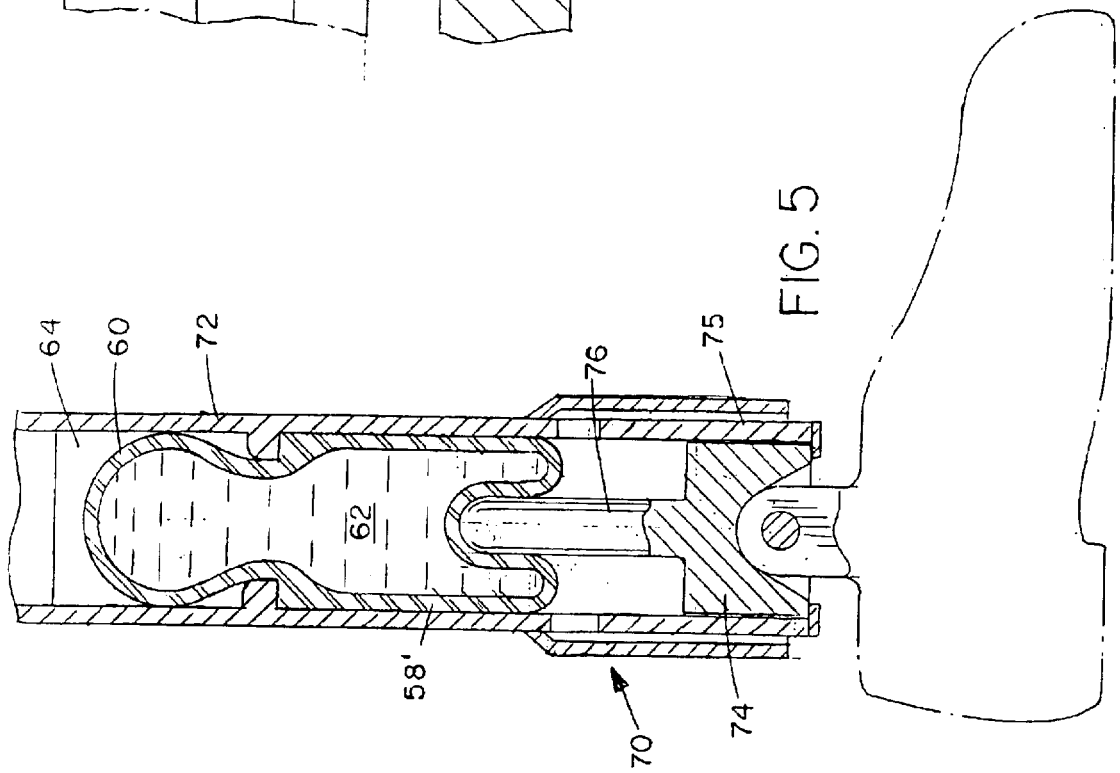

ATTENUATOR APPARATUS

CROSS REFERENCE TO RELATED APPLICATIONS

This application claims the benefit of priority of U.S. Provisional Application Ser. No. 60/311,318 filed Aug. 10, 2001 which is incorporated herein by reference in its entirety.

BACKGROUND OF THE INVENTION

The present invention relates to attenuators such as shock absorbers or energy management systems for absorbing or reducing shock or vibration forces produced by various devices, including vehicles, guns, heavy machinery, prosthetic devices, and electronic equipment.

A leg prosthesis, for example, is attached to the wearer's remaining limb, and a shock absorber or damping device is necessary for the wearer's comfort. Vehicles such as automobiles, bicycles, motor bikes and the like have shock absorbers or vibration damping mechanisms in their suspension system for a smoother ride. Guns also have recoil attenuators in order to reduce and/or modify the recoil energy on firing the gun. A firearm recoil attenuator is described in my U.S. Pat. No. 6,227,098. Most shock absorbing devices or energy attenuators use springs or resilient devices, or hydraulic means, to absorb the energy of an impact or the like.

SUMMARY OF THE INVENTION

It is an object of the present invention to provide a new and improved attenuator apparatus.

According to the present invention, an attenuator apparatus is provided which comprises a housing having a first chamber, a bellows member of elastomeric material mounted in the first chamber and having a second chamber filled with non-compressible fluid, the bellows member having a first end facing away from the first chamber, and a piston mounted in the housing at the first end of the bellows member for acting on the bellows member in a first direction in response to a force applied to the piston so as to expand the bellows member in the first chamber and cushion the force, whereby the bellows member returns to its original configuration and biases the piston back in a second direction opposite to the first direction on removal of the force.

The housing may be cylindrical and designed for mounting inside the tubular structure of a leg prosthesis, for example, adjacent a prosthetic knee joint. Alternatively, the apparatus may be incorporated in a recoil mechanism of a firearm, or in a heavy machine such as a press in order to absorb impact energy. There are many possible applications of this apparatus as an energy management device in a wide range of industrial and consumer products.

BRIEF DESCRIPTION OF THE DRAWINGS

The present invention will be better understood from the following detailed description of some exemplary embodiments of the invention, taken in conjunction with the accompanying drawings in which like reference numerals refer to like parts and in which:

FIG. 5 is a schematic illustration of the attenuator apparatus of FIG. 4 incorporated in a leg prosthesis;

FIG. 6 is a schematic illustration of the attenuator apparatus of FIG. 2 used as a dampener for a heavy press or other heavy equipment;

DETAILED DESCRIPTION OF THE DRAWINGS

Figure 1:
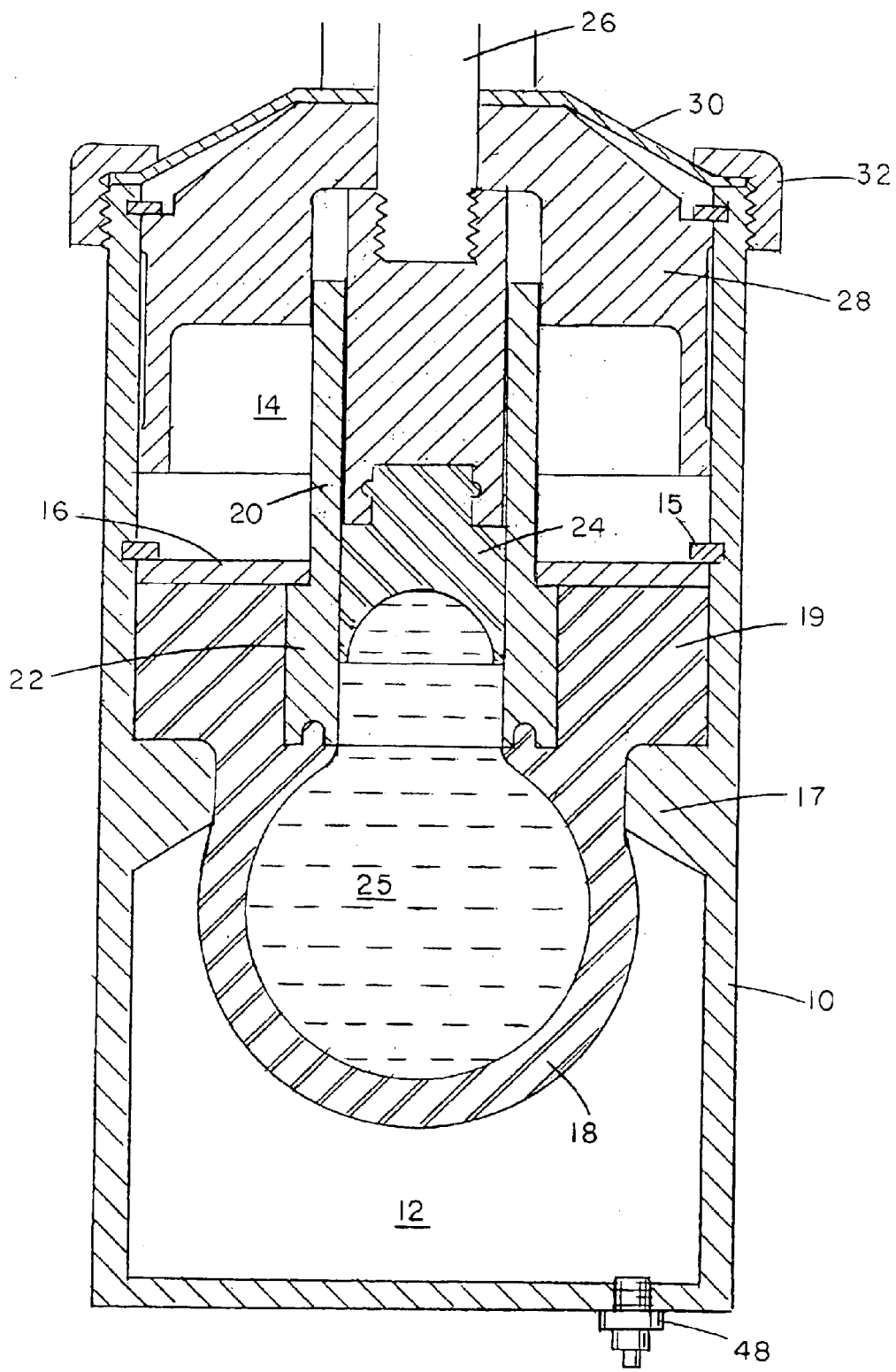
FIG. 1 is a cross-sectional view of an attenuator apparatus according to a first embodiment of the invention.

FIG. 1 of the drawings illustrates an attenuator apparatus according to a first embodiment of the invention. The apparatus basically comprises an outer body or housing 10 having a first or lower plenum chamber 12 and an upper chamber 14 separated from the first chamber 12 by dividing wall or brace 16, and a bulb-shaped bellows member 18 of elastomeric material having an upper, annular flange 19 secured between the wall 16 and an annular rib 17 in the chamber, with the bulb-shaped portion extending into the first chamber 12. A snap ring 15 secures the wall 16 and annular rim 19 against rib 17.

The wall 16 has a central opening through which a cylinder 20 extends, with a lower end of the cylinder secured in an upper end opening 22 of the bellows member 18. A piston 24 is slidably mounted in the cylinder 20. The bellows member 18 has an internal chamber 25 filled with hydraulic fluid, the hydraulic fluid filling both the chamber 25 and the portion of cylinder 20 beneath piston 24. The piston is secured to an actuator shaft or machine bolt 26 extending upwardly out of housing 10. A motion limiter 28 is secured in the upper end of chamber 14 to limit the movement of piston 24, with piston 24 being shown at the upper limit of its motion in FIG. 1. A sealing gasket 30 is secured over the upper end of housing 10 by an assembly cap 32 in order to keep water and foreign matter out of the attenuator.

The plenum chamber 12 is filled with a compressible gas via one-way fill valve 48, such that downward movement of piston 24 will be compensated by expansion of the bulb shaped elastomeric member 18, producing upward tension on the piston 24. When the downward force on piston 24 is released, it will be returned to its original position, illustrated in FIG. 1, since the elastomeric bellows member 18 will return to its original configuration, forcing the fluid in chamber 25 to move back up into the cylinder 20 to accommodate the reduction in size of chamber 25. Thus, the attenuator will act to absorb shocks or forces acting downwardly on member 26, and is a combined elastomeric, hydraulic, and pneumatic shock absorber.

The bellows member 18 is of a suitable elastomeric material such as urethane, nylon, latex materials or the like, which tend to return to their original shape repeatedly after stretching. The wall thickness, size of the chamber 25, and durometer hardness rating of the elastomeric material will be selected depending on the particular application and the forces likely to be encountered. Instead of filling the pneumatic chamber 12 with gas, the bulb 18 may alternatively be filled with gas and the chamber 12 may be filled with hydraulic fluid. In order to provide a larger expansion capacity, if required by the application, the chamber 25 may be made larger, or the piston and cylinder diameters may be increased. The shape of the bulb 18 in this embodiment is spherical, which has the advantage of providing the smallest possible surface area for a given volume. However, other bulb shapes may be used in alternative embodiments.

The attenuator or energy management apparatus is a cylindrical unit which can be readily fitted inside the tubular structure of a prosthesis. In order to assemble the unit, the bulb member 18 and cylinder 20 are filled with hydraulic fluid. The piston 24 is then inserted into the cylinder 20. The system is overfilled with fluid, so that the excess is compressed into the spherical chamber 25, causing the elastic bulb to expand under pressure, producing a preset upward tension on the piston. This preset tension keeps the piston in its upper position unless weight is applied. The motion limiter is then pushed below the rim of the housing, the sealing boot is aligned, and the cap is screwed on. The complete unit is then ready for service.

The plenum chamber 12 is filled with compressible gas such as air. The pressure in chamber 12 may be varied to accommodate different weights or forces on piston 24. For example, where the alternator is used to absorb shocks in a prosthetic device, higher pressures in chamber 12 will be used for heavier individuals, and the chamber 12 may be at a low pressure for a young child. The piston stroke will be of the order of 0.5 inches for a prosthetic application, but may vary in other applications. The proportions of the upper and lower chambers may be varied, along with the other parameters, in order to vary the expansion capacity.

The apparatus may be arranged as a combined hydraulic/pneumatic attenuator, or a hydraulic attenuator only, simply by varying the amount of gas in chamber 12. This makes the attenuator readily adaptable for a wide range of different applications, and different conditions in the same application, such as prosthetic device.

Figure 2:
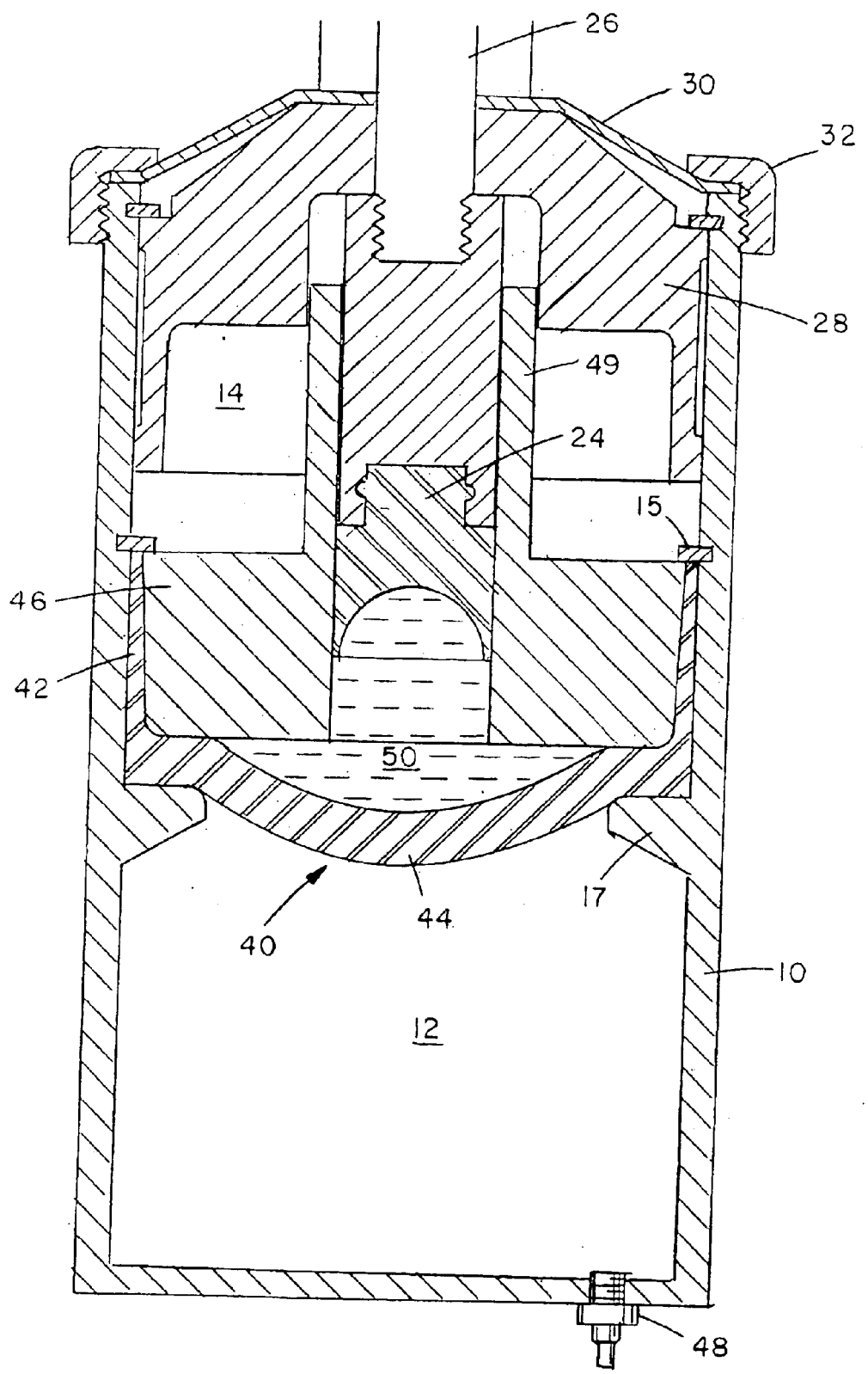
FIG. 2 is a cross-sectional view of an attenuator apparatus according to a second embodiment of the invention.

FIG. 2 illustrates a modified embodiment of the invention in which a different shape bellows member 40 is used, with a modified mounting arrangement. This embodiment is otherwise identical to that of FIG. 1, and like reference numerals have been used for like parts as appropriate. In this embodiment, the bellows member 40 is not bulb-shaped, but is a diaphragm or cup-shaped member with an upwardly directed, annular rim 42 and a slightly arcuate lower wall 44. The cylinder and dividing wall are not separate parts, as in the previous embodiment, but are formed as a single unit comprising an annular wall 46 having a central opening with an upwardly directed, cylindrical extension 49 in which the piston 24 is slidably mounted. The outer edge of the bellows member 40 is trapped between the wall 46 and annular rib 17 in the chamber 12, with the annular rim 42 trapped between the outer periphery of wall 46 and the inner surface of the housing 10. A snap ring 15 holds the assembly in position. A chamber 50 is formed between piston 24 and the arcuate wall 44 of the bellows member, and is filled with hydraulic fluid as in the previous embodiment.

The operation of the attenuator of FIG. 2 is exactly the same as in the previous embodiment, with downward force on the piston 24 causing it to move downwardly, compressing the fluid in chamber 50 downwardly, with the wall 44 expanding downwardly into chamber 12 to accommodate the downward movement of the piston without a change in the chamber volume. On removal of the force, the piston will be urged back upwardly into its original position, as the wall 44 returns to its original shape. This version will be easier and less expensive to manufacture than the bulb shaped elastomeric member of FIG. 1, but will have reduced flexibility and range of performance.

Figure 3:
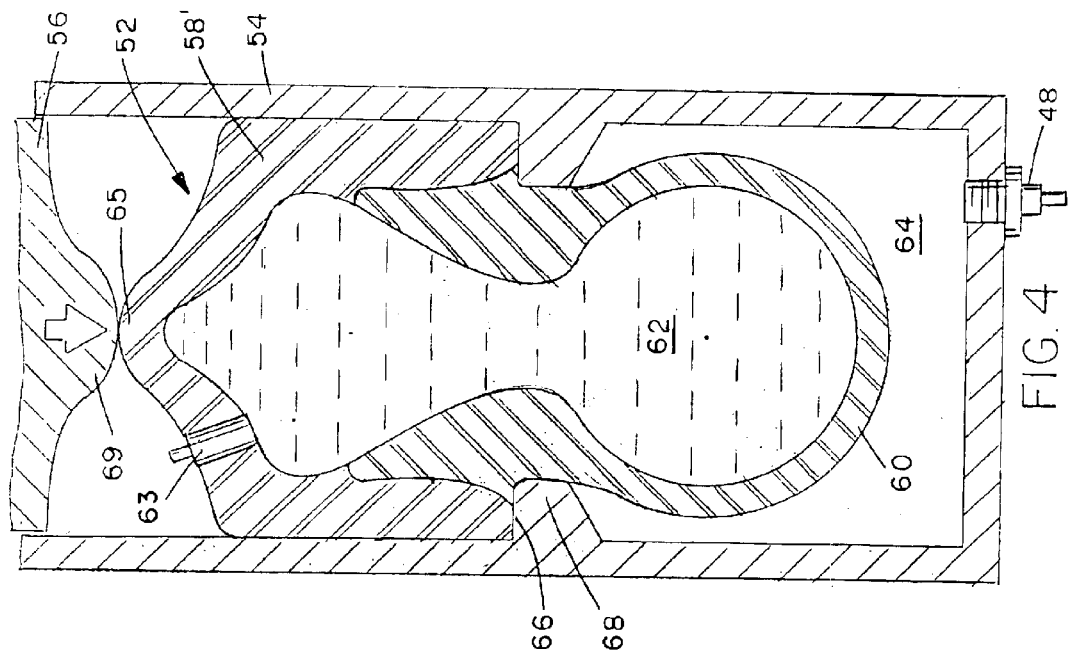
FIG. 3 is a cross-sectional view of an attenuator apparatus according to a third embodiment of the invention.

FIG. 3 illustrates another exemplary embodiment of the invention. In this version, instead of the piston forming an end wall of the bellows chamber and acting directly on the fluid in the chamber, a completely sealed bellows device 52 is mounted in an outer cylindrical housing 54, with a piston 56 slidably mounted in the housing above an upper end of the bellows device 52. The bellows device is formed in two parts 58,60 which are fused together to form a generally hourglass-shaped chamber 62 which is filled with hydraulic fluid. The wall of each part of the device 52 is formed of a suitable elastomeric material, and the lower, generally bulb-shaped part 60 projects downwardly into the lower plenum chamber 64 of the housing. The chamber 62 may be filled with hydraulic fluid using a syringe, self-sealing reed valve or poppet valve, or the like. The device 52 has a downwardly facing, annular rim or step 66 which is seated against an annular seat or rib 68 in the housing 54.

Downward force on the piston 56 in the direction of the arrow will tend to push the upper wall of the bellows chamber downwardly, forcing the fluid in chamber 62 downwardly and expanding the bulb-shaped lower portion 60 of the bellows device outwardly into chamber 64 to accommodate the reduction in volume at the upper end of the chamber. Thus, impacts will be absorbed by the expansion of the chamber wall and movement of the fluid. On removal of the force, the member 60 will return to its original configuration, forcing the upper member 58 upwardly and returning the piston to its original position.

Figure 4:
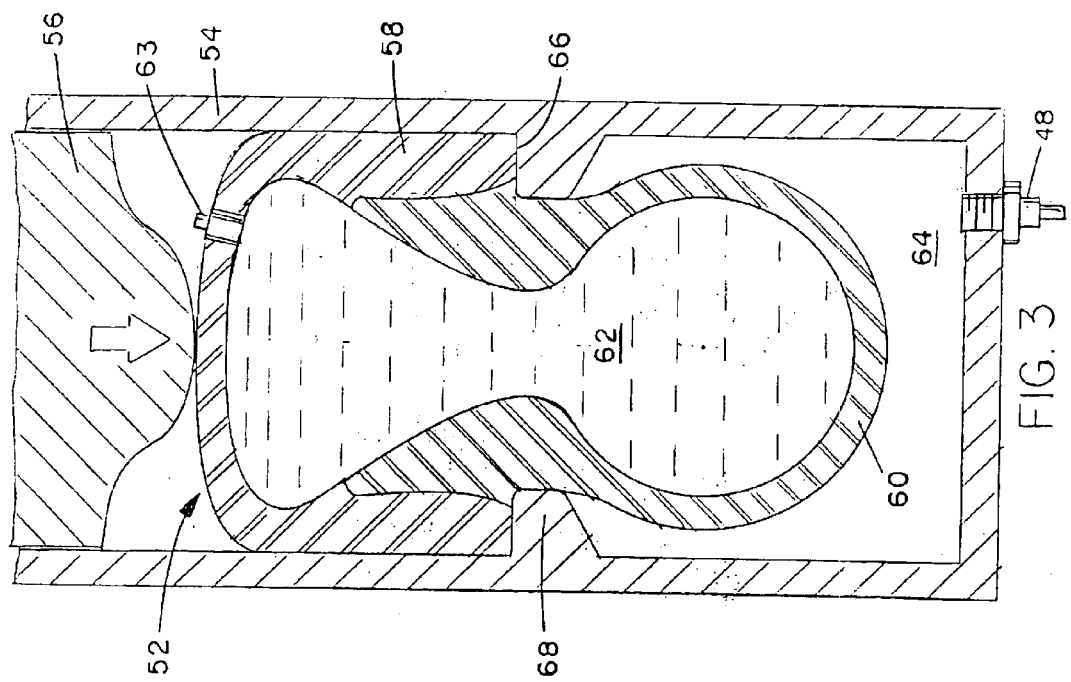
FIG. 4 is a cross-sectional view of an attenuator apparatus according to a fourth embodiment of the invention.

FIG. 4 illustrates a modification of the embodiment of FIG. 3, in which like reference numerals have been used for like parts. In this embodiment, the shape of the upper part 58' of the bellows device has been modified, to provide an upward bulge or arched portion 65 at the center of the upper wall, which acts against a correspondingly shaped central portion 69 of the piston 56. This shaped portion of the bellows member will be more readily compressible downwardly on downward force being applied by piston 56, and will tend to reverse itself in the manner of a sock being turned inside out. It will also return more readily to its original configuration on removal of force. As in the previous embodiment, chamber 62 is filled using a syringe through a self-sealing reed valve 63.

The attenuator apparatus or energy management device of this invention is particularly suitable for use as a shock absorber in prosthetic devices such as prosthetic legs, and can be readily installed in a tubular portion of such devices. Attenuator units having a range of different preset tensions may be provided, for use by different weight individuals. In this way, a prosthetic leg for use by a child can be readily upgraded with attenuator units of different weight ratings as the child grows, or by varying pressure in chamber 12, as discussed above. This device will provide increased comfort and improved function of a leg prosthesis.

Although primarily designed for use in a prosthetic device, the invention can be readily adapted for use in a wide range of alternative fields where energy management is an issue, such as firearms, bicycles, vehicles, electronic equipment and instrumentation which is vibration sensitive, and heavy machinery. A number of the attenuators may be arranged at spaced intervals around the periphery of the floor of a heavy press, for example. Other possible applications include shock absorbers for bicycle forks, car door closing dampers, automobile suspension damping, and the like. Some examples of possible uses of the attenuator are illustrated in FIGS. 5 to 11.

FIG. 5 illustrates one possible application of the attenuator apparatus of FIG. 4 in a telescoping joint of a leg prosthesis 70. As illustrated in FIG. 5, the bellows device is installed in a bore in the upper cylinder 72 of the telescoping joint. Piston 74 is mounted in the lower cylinder 75 of the telescoping joint, and has an actuator rod 76 which engages the upper part 58' of the bellows device. As the wearer of the prosthesis walks, downward force will be applied and the upper cylinder will move downwardly over the lower cylinder 75, such that the bulb-shaped portion 60 of the bellows device will expand in chamber 64, cushioning the force and tending to return the upper cylinder upwardly when the force is removed.

FIG. 6 illustrates an example of the attenuator device of FIG. 2 used as one of a plurality of identical dampeners 80 for the floor 82 of a heavy press 84. As illustrated, the housing 10 is installed in a hole in floor 82 with actuator shaft 26 extending upwardly through compressible pad 85 positioned beneath the press. Impact energy will be absorbed by expansion of diaphragm 44 into chamber 12. A plurality of such dampeners 80 will be installed at spaced intervals around the periphery of the press, providing significant dampening and energy absorption.

Figure 7:
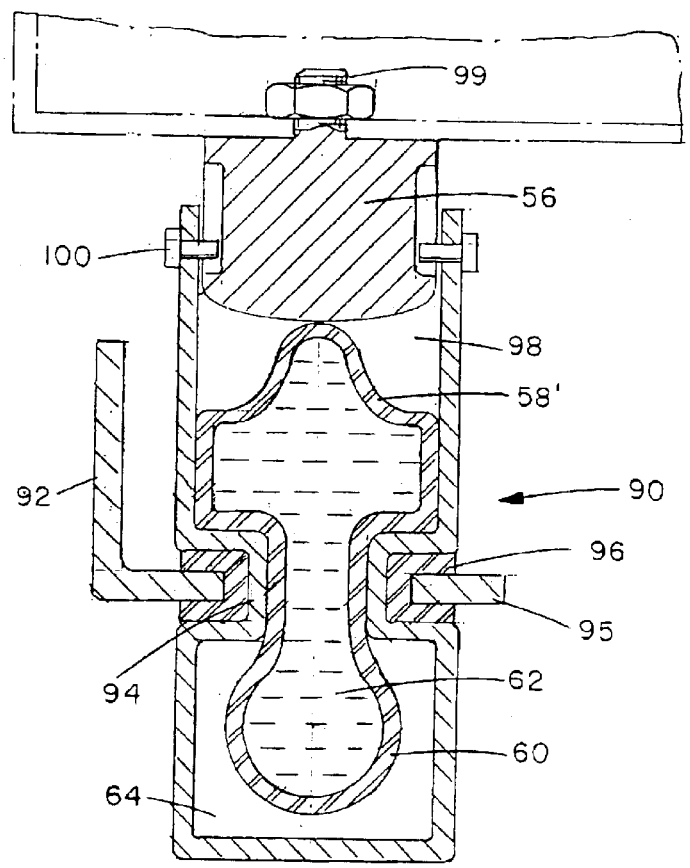
FIG. 7 is a schematic cross sectional view of the attenuator apparatus of FIG. 4 used as a high frequency damper for electronics equipment.

Another possible use for the attenuator apparatus of FIG. 4 is illustrated in FIG. 7. In this case, a plurality of the attenuator units may be installed as dampeners 90 around the periphery of the chassis of electronics equipment to support the equipment within a housing 92. The outer housing 54 of the apparatus is modified to include a reduced diameter neck 94 extending through an opening in the base 95 of the housing, with a shock absorbent washer or grommet 96 between the neck 94 and the base opening. The housing has a lower chamber 64 below the neck into which the bulb-shaped part 60 of the bellows device extends, and an upper chamber 98 above the neck in which the upper part 58' of the bellows device is located. Piston member 56 is slidably mounted in the chamber 98 above part 58', and has a screw fastener 99 at its upper end for connection to the chassis of the electronics racked equipment (illustrated in dotted outline). A snap ring 100 will control the amount of movement of piston 56. A plurality of such dampeners 90 will be installed at suitable intervals around the chassis. This will act to reduce shocks and vibrations, and will be helpful for equipment which is vibration sensitive.

Figure 8:
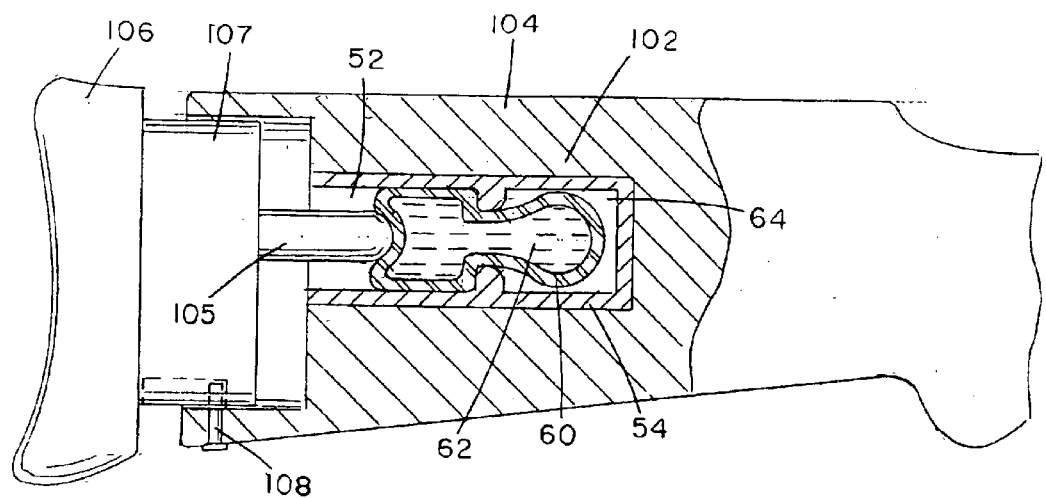
FIG. 8 is a schematic view of the attenuator apparatus of FIG. 3 used as a recoil softener.

FIG. 8 illustrates use of the attenuator apparatus of FIG. 3 as a recoil softener unit 102 in the butt stock 104 of a shotgun or rifle. An actuator rod 105 projects from the shoulder pad 106 to engage the end wall of bellows device 52, so that firing of the firearm will tend to force the rod 105 inwardly into housing 54, forcing the bulb-shaped portion 60 of the bellows to expand in chamber 64, softening the recoil. The shoulder pad has an extension 107 which slides in a bore 108 in the butt end 104 of the gunstock, and a recoil limiting pin 108 on the butt engages a slot in extension 107.

Figure 9:
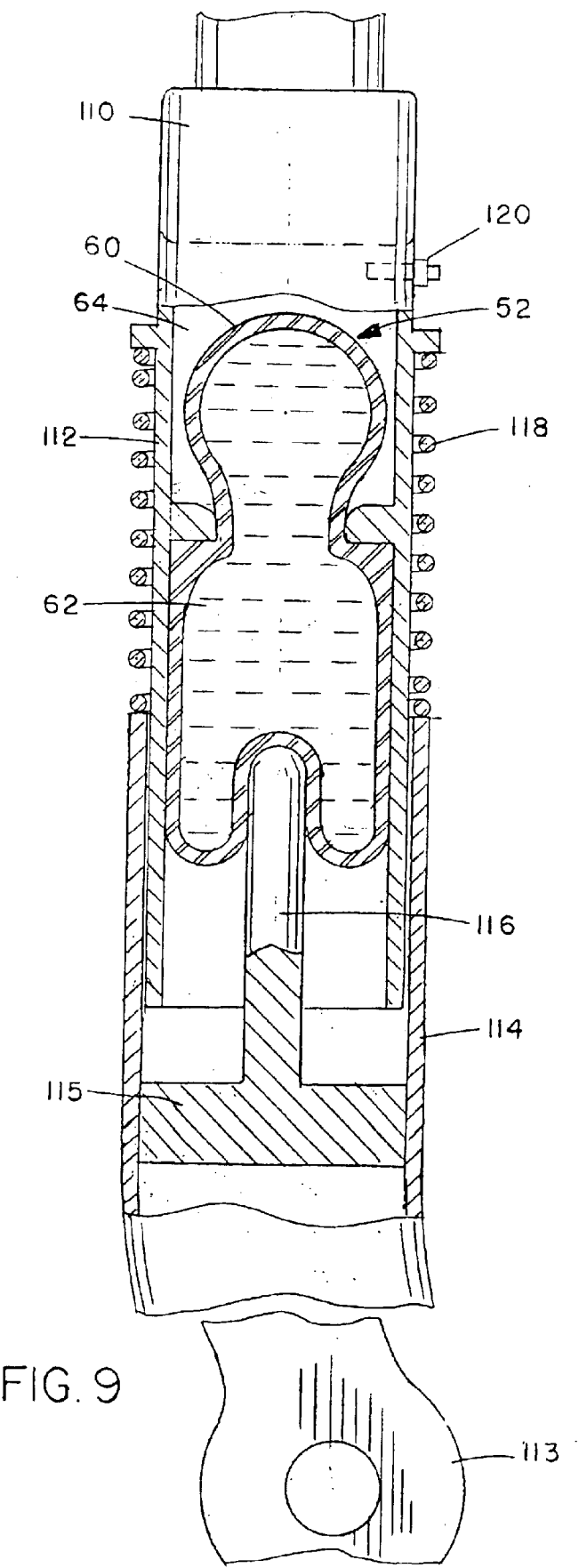
FIG. 9 is a schematic illustration of the attenuator apparatus of FIG. 3 used as a shock absorber in a bicycle strut.

FIG. 9 illustrates the use of an attenuator apparatus of the type illustrated in FIGS. 3 and 4 as a shock absorber in a telescoping joint on the front fork 110 of a bicycle strut. The bellows device 52 is mounted directly in a first cylinder 112 which is telescopically mounted in second cylinder 114. Piston 115 is secured in the second cylinder 114 and has an actuator rod 116 projecting into the open end of inner cylinder 112 and engaging the end of the bellows device 52. Cylinder 114 is connected to wheel lug 113. The opposite end of the bellows device comprises the bulb-like portion 60 and projects into a plenum chamber 64 provided in cylinder 112. A return spring 118 is provided to return cylinder 112 into the extended condition. Force applied to the wheel lug 113 will tend to force cylinder 114 upwardly into cylinder 112, such that rod 116 moves further inwardly, deforming the end wall of the bellows device 52. This also forces fluid in chamber 62 into bulb-shaped portion 60, expanding it outwardly and attenuating the shock, as described above in connection with FIG. 3. Air valve 120 is provided in cylinder 112 to vary the gas pressure in the cylinder.

Figure 10:
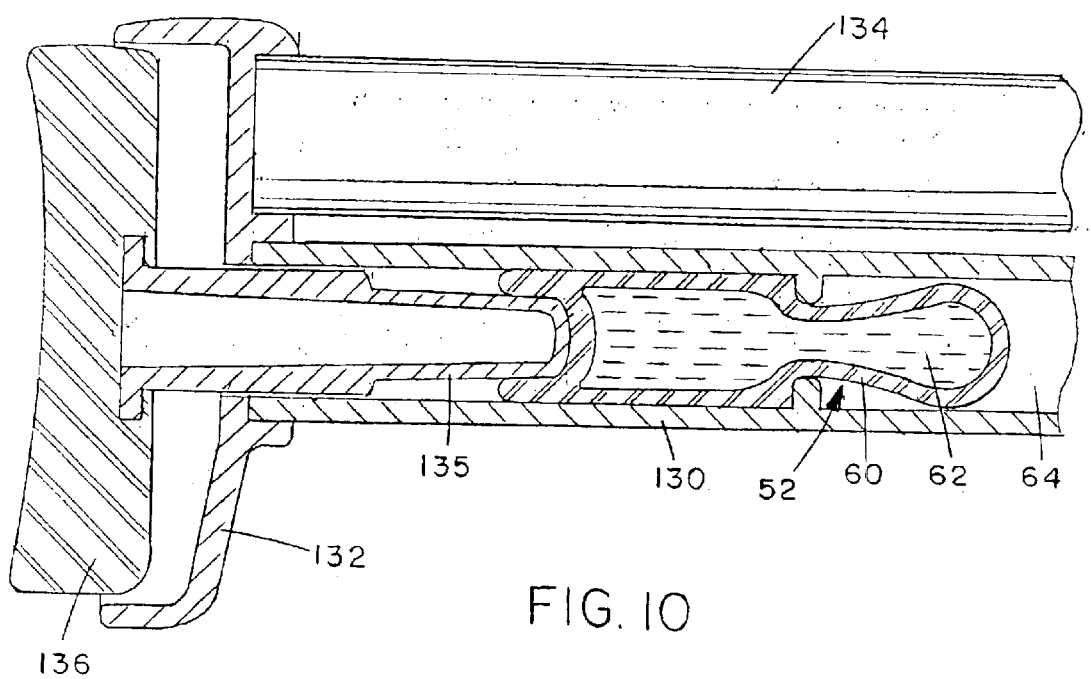
FIG. 10 is a schematic cross-sectional view of the attenuator apparatus of FIG. 3 used as an attenuator PTO for an automatic or assault rifle.

FIG. 10 illustrates use of the device of FIG. 3 as a shock absorber in an automatic or assault rifle which does not have a regular stock. Bellows device 52 is mounted in lower stock tube 130 projecting from the butt 132 of the rifle below the upper stock tube 134. The dual tubes may alternatively be designed as a folding stock, as is well known in the field. A projection 135 from the shoulder pad 136 extends into the barrel 130 and acts against one end of the bellows device 52, which is filled with hydraulic fluid 62. The opposite end or bulb-shaped portion 60 of the bellows device extends and expands into chamber 64 which is filled with pressurized gas, as discussed above in connection with FIG. 3.

Figure 11:
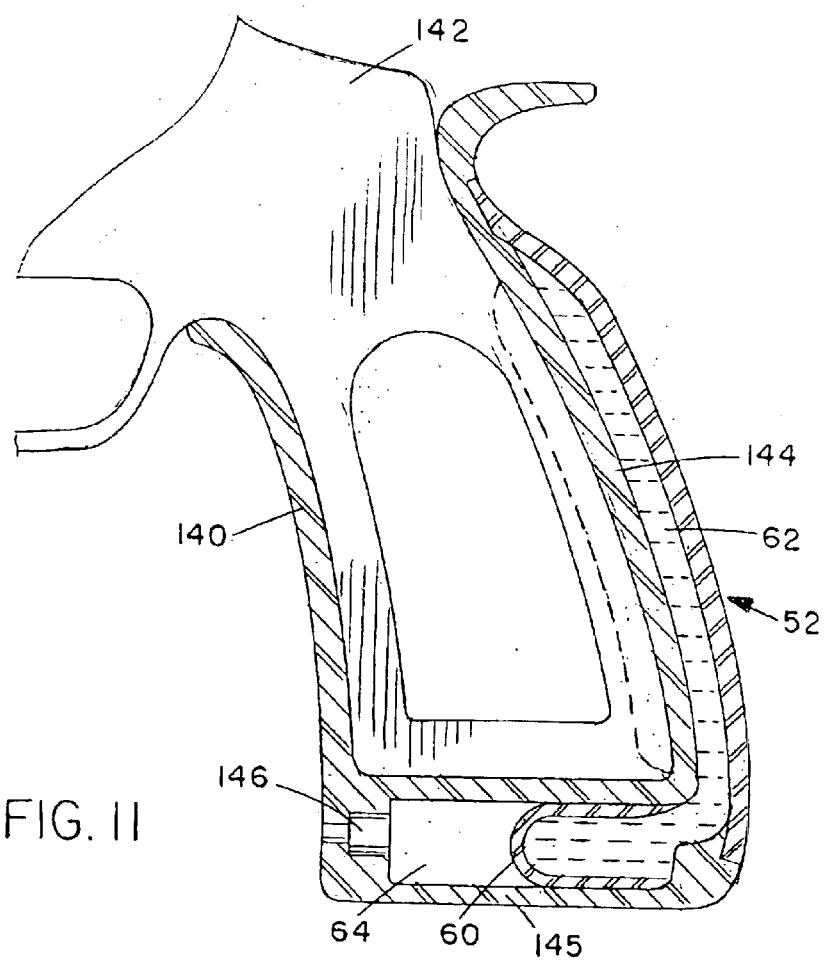
FIG. 11 is a schematic cross-sectional view illustrating the attenuator incorporated in the grip of a handgun.

Finally, the embodiment of FIG. 11 illustrates use of the device as a shock absorber or recoil attenuator in the grip 140 of a revolver. The device could be adapted also for use in a semi-automatic pistol. The metal frame 142 of the revolver extends into the grip 140 in a conventional manner. The bellows device 52 is mounted to wrap around the back strap 144 of the revolver and is blended into the outer wall of the grip as indicated. Air or gas chamber 64 is provided in the base 145 of the grip, and an air filler valve 146 is provided to adjust the air pressure and thus the required shock absorption. A portion 60 of the bellows device extends into the chamber 64 as indicated. Recoil of the metal frame on firing the revolver will therefore tend to deform the inner wall of the bladder (indicated in dotted outline), expanding the portion 60 of the bladder extending into base chamber 64 to absorb shock, reducing the recoil effect.

From the foregoing, it is clear that the attenuator apparatus of this invention is readily adaptable to a large number of different applications, from dampening vibrations in electronics equipment, absorbing shocks in the floor or base of heavy machinery such as heavy presses, to softer dampening for softening firearm recoil and impact when walking on a leg prosthesis. Various parameters of the apparatus may be varied to provide a greater or lesser amount of shock absorption, such as the pressure in the plenum chamber 12 or 64, varying the size of the chamber in the bellows device, varying the durometer hardness of the elastomeric material used for the bellows device, varying the piston and cylinder diameters, and so on. This apparatus therefore has many possible applications as an energy management device in a wide variety of fields.

Although some exemplary embodiments of the invention have been described above by way of example only, it will be understood by those skilled in the field that modifications may be made to the disclosed embodiments without departing from the scope of the invention.

What is claimed is:

1. A shock absorbing apparatus for reducing shock as a result of an applied force, the apparatus comprising:
   a housing having a first end and a second end;
   a bellows device mounted in the housing and dividing the housing into a first chamber between the first end and bellows device, and a second chamber between the bellows device and the second end;

the second chamber being filled with a first fluid;

the bellows device having at least a portion extending into said second chamber which is made entirely of a non-metallic, elastomeric material, and forming a third chamber which is filled with a second fluid, the third chamber having a first end facing away from the second chamber;

a piston slidably mounted in the first chamber and acting on the first end of the third chamber in a first direction in response to a force applied to the piston so as to expand the portion of the bellows device extending into said second chamber and cushion the force, whereby the bellows device returns to its original configuration and biases the piston back in a second direction opposite to the first direction on removal of the force.

2. The apparatus as claimed in claim 1, wherein at least one of the fluids is a liquid.

3. The apparatus as claimed in claim 1, wherein one of the fluids is a liquid and the other fluid is a compressible gas.

4. The apparatus as claimed in claim 1, wherein the bellows device is of generally spherical shape.

5. The apparatus as claimed in claim 1, wherein a cylinder extends from the first end of the housing and has a second end spaced from the second end of the housing, the bellows member having an upper, open end secured to the second end of the cylinder, the piston is being slidably mounted in the cylinder to close the upper open end of the bellows member, and an actuator shaft is secured to the piston and extends out through the first end of the housing for attachment to a device to be damped, whereby the piston acts directly on the fluid in said third chamber.

6. The apparatus as claimed in claim 1, wherein the bellows member comprises a generally arcuate diaphragm extending across the housing and forming an end wall of said first chamber, said second chamber extending from said end wall to the second end of said housing, and a cylinder extends from the first end of the housing towards said diaphragm, the piston being slidably mounted in the cylinder and an actuator shaft extending from the piston through the first end of said housing, the cylinder having an end wall, the end wall and piston together forming a closure for said third chamber between said diaphragm and end wall, whereby the piston acts directly on fluid in said third chamber.

7. The apparatus as claimed in claim 1, wherein the bellows member forms a completely sealed chamber having a deformable end wall, the second chamber being located between said bellows member and said second end of said housing, the piston being slidably mounted in said housing between said first end and said deformable end wall and acting on said end wall, and an actuator shaft extending from said piston through the first end of said housing, whereby force applied to the piston will force the piston towards the second end of said housing, pushing the deformable end wall inwardly into said third chamber and expanding the bellows member.

8. The apparatus as claimed in claim 1, wherein the first end of the third chamber comprises an end wall having an opening communicating with said third chamber, and the housing has a cylinder extending from said first end to said end wall opening, said piston being slidably mounted in said cylinder and acting directly on the second fluid in said third chamber.

9. The apparatus as claimed in claim 1, wherein said first fluid is a compressible gas and the second fluid is a hydraulic fluid.

10. A shock absorbing apparatus for reducing shock as a result of an applied force, the apparatus comprising:

a housing having a first end and a second end;

a bellows device mounted in the housing and dividing the housing into a first chamber between the first end and bellows device, and a second chamber between the bellows device and the second end;

the second chamber being filled with a first fluid;

the bellows device having at least a portion extending into said second chamber which is of elastomeric material, and forming a third chamber which is filled with a second fluid, the third chamber having a first end facing away from the second chamber;

a piston slidably mounted in the first chamber and acting on the first end of the third chamber in a first direction in response to a force applied to the piston so as to expand the portion of the bellows device extending into said second chamber and cushion the force, whereby the bellows device returns to its original configuration and biases the piston back in a second direction opposite to the first direction on removal of the force; and the first end of the third chamber comprising a deformable, closed end wall of said bellows device, and said piston acts directly on said closed end wall.

11. A shock absorbing assembly, comprising:

a device having a first part and a second part movable relative to the first part on application of a force;

an attenuator apparatus mounted at a joint between the first and second parts; and the attenuator apparatus comprising a housing having a first end and a second end, a bellows member mounted in the housing and dividing the housing into a first chamber between the first end and bellows member, and a second chamber between the bellows member and the second end, the second chamber being filled with a first fluid, the bellows member having at least a portion extending into said second chamber which is made entirely of a non-metallic, elastomeric material, and forming a third chamber having a first end facing away from the second chamber, and a piston secured to the first part and slidably mounted in said first chamber for acting on the first end of the third chamber in a first direction in response to application of a force to said device so as to expand the portion of the bellows member extending into the second chamber and cushion the force, whereby the bellows member returns to its original configuration and biases the piston back in a second direction opposite to the first direction on removal of the force.

12. The assembly as claimed in claim 11, wherein the device comprises a leg prosthesis.

13. The assembly as claimed in claim 11, wherein the device comprises a bicycle front fork.

14. The assembly as claimed in claim 11, wherein the device comprises a firearm.

15. The assembly as claimed in claim 11, wherein the device comprises an electronics equipment chassis.

* * * * *